(12) United States Patent
Landry

(10) Patent No.: US 6,423,525 B1
(45) Date of Patent: Jul. 23, 2002

(54) ISOLATION AND COMPOSITION OF A NOVEL GLYCOSIDASE FROM CHRYSEOBACTERIUM

(75) Inventor: David Landry, Essex, MA (US)

(73) Assignee: New England Biolabs, Inc., Beverly, MA (US)

( * ) Notice: Subject to any disclaimer, the term of this patent is extended or adjusted under 35 U.S.C. 154(b) by 76 days.

(21) Appl. No.: 09/859,698

(22) Filed: May 17, 2001

Related U.S. Application Data

(60) Division of application No. 09/428,979, filed on Oct. 28, 1999, which is a continuation-in-part of application No. 08/560,809, filed on Nov. 21, 1995, now Pat. No. 6,300,113, which is a continuation-in-part of application No. 08/596,250, filed as application No. PCT/US94/10758 on Sep. 22, 1994, now Pat. No. 5,770,405.

(51) Int. Cl.$^7$ .................................................. C12N 9/24
(52) U.S. Cl. ....................... 435/200; 435/69.1; 435/183; 435/195; 435/201; 435/252.3; 435/320.1; 536/23.2
(58) Field of Search ............................... 435/69.1, 183, 435/195, 200, 201, 320.1, 252.3; 536/23.2

(56) References Cited

U.S. PATENT DOCUMENTS

| | | | |
|---|---|---|---|
| 5,258,295 A | 11/1993 | Starr et al. ................ | 435/172.3 |
| 5,258,304 A | * 11/1993 | Carpenter et al. .......... | 435/264 |
| 5,610,063 A | 3/1997 | Smith et al. ............ | 435/254.23 |

FOREIGN PATENT DOCUMENTS

| | | |
|---|---|---|
| DE | 3326546 | 2/1985 |
| EP | 0 324 399 | 7/1988 |
| JP | 06217769 | 8/1994 |
| WO | WO91/05256 | 4/1991 |
| WO | WO92/02816 | 2/1992 |
| WO | WO93/04074 | 3/1993 |
| WO | WO93/05076 | 3/1993 |

OTHER PUBLICATIONS

Hayward, J. Appl. Bacteriol. 43:407–412 (1977).
Glover, "Gene Cloning. The Mechanics of DNA Manipulation" 1984 by Chapman and Hall (London) pp. 1–20.
Kawasaki, et al., J. of Biological Chemistry 252:6536–6543 (1977).
Mizuochi, et al., J. of Biological Chemistry 253:7404–7409 (1978).
Sasaki, et al., J. of Biological Chemistry, 262:12059–12076 (1987).
Kagawa, et al., J. of Biological Chemistry, 263:17508–17515 (1988).
Parekh, et al. Biochemistry, 28:7644–7662 (1989).
Parekh, et al., Biochemistry, 28:7670–7679 (1989).
Wittwer, et al., Biochemistry, 28:7662–7669 (1989).
Barton, et al., Proc. Natl. Acad. Sci. 87:1913–1916 (1990).
Parekh, et al., European J. of Biochemistry, 203:135–141 (1992).
Rice, et al., Analytical Biochemistry, 206:278–287 (1992).
Lund, et al., Human Antibody Hybridomas, 4:20–25 (1993).
Galili, et al., Proc. Natl. Acad. Sci., 84:1369–1373 (1987).
Galili, et al., J. of Biological Chemistry 263:17755–17762 (1988).
Lund, et al., Human Antibody Hybridomas, 4:20–25 (1993).
Dube, et al., J. Biological Chemistry, 33:17516–17521 (1988).
Moremen, et al. J. of Biological Chemistry, 266:16876–16885 (1991).
Sheares, et al., Proc. Natl. Acad. Sci., USA, 83:1993–1997 (1986).
Edge, et al., Nature, 358:693–694 (1992).
Landers, et al., BioTechniques, 14:98–108 (1993).
AAAS 1993 Meeting (Boston, MA) Seminar Concurrent Discussion Carbohydrate Structure Analysis & Glycobiology.
Edge, et al., Proc. Natl. Acad. Sci., 89:6338–6342 (1992).
Jackson, Biochemistry Journal, 270:705–713 (1990).
Turnbull and Gallagher, Biochem. J. 251:597–608 (1988).
Parekh, et al., The EMBO Journal, 6:1233–1244 (1987).
Wang, et al., Analytical Biochemistry, 141:366–381 (1984).
Prakash and Vijay, Analytical Biochemistry, 128:41–46 (1983).
Baenziger and Maynard, J. of Biological Chemistry, 255:4607–4613 (1980).
Wang, et al., Analytic Biochemistry, 141:366–381 (1984).
Reinhold, et al., J. Carbohydrate Chemistry, 2:1–18 (1983).
Wells, et al., Analytical Biochemistry, 110:397–406 (1981).
Tronsmo and Harman, Analytical Biochemistry, 208:74–79 (1993).
Young, et al., Biochemistry, 10:3457–3460 (1971).
Yamashita, et al., Methods in Enzymology, 83:105–126 (1982).
Yamashita, et al., J. of Biological Chemistry, 255:5635–5642 (1980).

(List continued on next page.)

Primary Examiner—Nashaat T. Nashed
Assistant Examiner—Christian L. Fronda
(74) Attorney, Agent, or Firm—Gregory D. Williams

(57) ABSTRACT

In accordance with the present invention, there are provided substantially pure glycosidases obtainable from the genus Chryseobacterium. In particular, there is provided a substantially pure exo α-N-Acetylgalactosaminidase from Chryseobacterium meningosepticum. A method of cloning this enzyme and producing a recombinant form of the enzyme is also provided by the present invention.

6 Claims, 3 Drawing Sheets

OTHER PUBLICATIONS

Fukuda, Biochemistry, 24:2154–2163 (1985).
Turco, et al., Analytical Biochemistry, 118:278–283 (1981).
Camirand, et al., J. of Biological Chemistry, 266:15120–15127 (1991).
Umemoto, et al., J. Biol. Chem. 252:8609–8614 (1977).
Bhavanandan, et al., Biochemical and Biophysical Research Communications, 70:738–745 (1976).
Glasgow, et al., J. Biol. Chem. 252:8615–8623 (1977).
Vliegenthart, et al., Advances in Carbohydrate Chemistry And Biochemistry, 41:209–375 (1983).
Flowers and Sharon, Adv. Enzymol., 48:29–95 (1979).
Kobata, Department of Biochemistry, The Institute of Medical Science. The University of Tokyo, Japan, "The Carbohydrates of Glycoproteins", pp. 87–161 (1982).
Dell, Advances in Carbohydrate Chemistry and Biochemistry 45:19–72 (1987).
Conzelmann and Sanhoff, Adv.Enzymol. 60:89–216 (1987).
Rademacher, et al., Ann. Rev. Biochem., 57:785–838 (1988).
Dahms, et al., J. of Biological Chemistry, 264:12115–12118 (1989).
Paulson, TIBS, 14:272–276 (1989).
Spellman, Anal. Chem., 62:1714–1722 (1990).
Lee, et al., Applied Biochemistry and Biotechnology, 23:53–80 (1990).
Cumming, Glycobiology, 1:115–130 (1991).
Ichikawa, et al., Analytical Biochemistry, 202:215–238 (1992).
Geisow, Bio/Technology, 10:277–280 (1992).
Edge, et al., Nature, 358:695 (1992).
Edge, et al., Nature, 358:693–694 (1992).
Stanley, Glycobiology, 2:99–107 (1992).
Varki, et al., Glycobiology, 3:97–130 (1993).
Harris and Spellman, Glycobiology, 3:219–224 (1993).
Spellman, Anal. Chemi. 62:1714–1722 (1990).
Kobata, Anal. Chem. 100:1–14 (1979).
Schatzle, et al., J. of Biological Chemistry 267:4000–4007 (1992).
Daniel, et al., Glycobiology, 2:327–336 (1992).
DeGasperi, et al., J. of Biological Chemistry, 267:9706–9712 (1992).
Tulsiani, et al., J. of Biological Chemistry, 257:3660–3668 (1982).
Opheim, et al., J. of Biological Chemistry, 253:1017–1023 (1978).
Tulsiani, et al., Archives of Biochemistry and Biophysics, 267:60–68 (1988).
Phillips, et al., Biochemistry J., 153:579–587 (1976).
Tulsiani, et al., J. of Cell Biology, 109:1257–1267 (1989).
Yamamoto, et al., Agr. Biol. Chem. 39:1981–1988 (1975).
Yamamoto, et al., J. of Biochem. 91:1971–1979 (1982).
Tulsiani, et al., J. of Biological Chemistry, 260:13081–13087 (1985).
Bonay, Eur. J. Biochem. 197–229–238 (1991).
Tabas, et al., J. of Biological Chemistry, 254:11655–11663 (1979).
Tulsiani, et al., J. of Biological Chemistry, 252:3227–3233 (1977).
Kaushal, et al., Biochemistry, 29:2168–2176 (1990).
Shoup, et al., J. of Biological Chemistry, 251:3845–3852 (1976).
Snaith, et al., Biochem. J. 117:129–137 (1970).
Bischoff, et al., J. of Biological Chemistry, 258:7907–7910 (1983).
Yamashita, et al., Biochemical and Biophysical Research Communications 96:1335–1342 (1980).
Kobata, et al., Methods in Enzymology, 138:779–785 (1987).
Swaminathan, et al., J. of Biological Chemistry, 247:1775–1779 (1972).
Matta, et al., J. of Biological Chemistry, 247:1780–1787 (1972).
Okumura, et al., Methods Enzym. 28:792–796 (1972).
Ichishima, et al., Biochimica et Biophysica Acta 658:45–53 (1981).
Sopher, et al., Biochem. J. 289:343–347 (1993).
Toyoshima, et al. Biochemical and Biophysical Research Communications 51:945–950 (1973).
Li and Lee, J. of Biological Chemistry, 247:3677–3683 (1972).
Aminoff and Furukawa, J. of Biological Chemistry, 245:1659–1669 (1970).
Carlsen and Pierce, J. of Biological Chemistry, 247:23–32 (1972).
Opheim and Touster, J. of Biological Chemistry 252:739–743 (1977).
DiCioccio, et al., J. of Biological Chemistry 257:714–718 (1982).
Scudder, et al., J. of Biological Chemistry 265:16472–16477 (1990).
Sano, et al. J. of Biological Chemistry 267:1522–1527 (1992).
DeGasperi, et al., J. of Biological Chemistry, 267:9706–9712 (1992).
Butters, et al. Biochem. Journal, 279:189–195 (1991).
"alpha1, 2–L–Fucosidase From Arthrobacter oxidans F1" Takara Biochemicals, Takara Shuzo Co., Ltd.
Yoshima, et al., Arch. of Biochem. and Biophysics 194:394–398 (1979).
Bahl, J. of Biological Chemistry 245:299–304 (1970).
Ogata–Arakawa, et al., Arch. of Biochem. and Biophy. 181:353–358 (1977).
Furukawa and Aminoff, Fed. Proc. 28:606 (1969).
Kochibe, J. Biochem. 74:1141–1149 (1973).
Suzuki, et al., J. of Biological Chemistry 245:781–786 (1970).
Distler and Jourdian, J. of Biological Chemistry, 248:6772–6780 (1973).
Haibach, et al. Biochem. and Biophysical Research Communications 181:1564–1571 (1991).
Dean and Sweeley, J. of Biological Chemistry, 254:9994–10000 (1979).
Dey, Eur. J. Biochem., 140:385–390 (1984).
Suzuki, et al., J. of Biological Chemistry 245:781–786 (1970).
Williams, et al., Biochem. J. 175:1069–1077 (1978).
Gherardini, et al., J. of Bacteriology, 161:500–506 (1985).
Itoh, et al., Agric. Biol. Chem., 43:1499–1504 (1979).
Li and Shetlar, Arch. of Biochem. and Bioph. 108:523–530 (1964).
Dey and Pridham, Biochem. J. 113:49–55 (1969).
Yates, et al., FEBS Letters, 60:281–285 (1975).
Furukawa and Aminoff, Fed. Proc. 28:606 (1969).
Kochibe, J. Biochem. 74:1141–1149 (1973).
Suzuki, et al., J. of Biological Chemistry 245:781–786 (1970).

Distler and Jourdian, J. of Biological Chemistry, 248:6772–6780 (1973).
Haibach, et al. Biochem. and Biophysical Research Communications 181:1564–1571 (1991).
Dean and Sweeley, J. of Biological Chemistry, 254:9994–10000 (1979).
Dey, Eur. J. Biochem., 140:385–390 (1984).
Suzuki, et al., J. of Biological Chemistry 245:781–786 (1970).
Williams, et al., Biochem. J. 175:1069–1077 (1978).
Gherardini, et al., J. of Bacteriology, 161:500–506 (1985).
Itoh, et al., Agric. Biol. Chem., 43:1499–1504 (1979).
Li and Shetlar, Arch. of Biochem. and Bioph. 108:523–530 (1964).
Dey and Pridham, Biochem. J. 113:49–55 (1969).
Yates, et al., FEBS Letters, 60:281–285 (1975).
Zapater, et al. Preparative Biochemistry, 20:263–296 (1990).
Yu–Teh, et al., J. of Biological Chemistry, 242:5474–5480 (1967).
Jones and Ballou, J. of Biological Chemistry 244:1043–1051 (1969).
Sukeno, et al., Methods Enzymol., 28:777–782 (1972).
Okumura, J. Biochem. 73:131–138 (1973).
Shigeta, et al., J. Biochem., 84:1827–1832 (1983).
Paus and Christensen, Eur. J. Biochem., 25:308–314 (1972).
Saita, et al. J. Biochem., 70P:827–833 (1971).
Tulsiani, et al., Biochem. J. 290:427–436 (1993).
Every and Ashworth, Biochem. J. 133:37–47 (1973).
Snaith and Levvy, Biochem. J. 114:25–33 (1969).
Ziegler and Trimble, Glycobiology 1:605–614 (1991).
Sugahara, et al., Methods Enzym. 28B:769–772 (1992).
McCabe, et al. Biochimica et Biophysica Acta 1077:133–140 (1991).
Sone, et al., J. Biochem., 83:1135–1144 (1978).
Bouquelet, et al., Biochimica et Biophysica Acta 522:521–530 (1978).
Shah and Parekh, Indian J. of Biochem and Biophy. 27:103–107 (1990).
Li and Li, Methods Enzymol. 28:714–720 (1972).
Malhotra and Dey, Biochem. J. 103:508–513 (1967).
Talbot and Sygusch, Appl. and Environ. Microbiology, 56:3505–3510 (1990).
Oishi, et al., Agr. Biol. Chem., 36:578–587 (1972).
Kaji, et al., Agr. Biol. Chem. 36:1335–1342 (1972).
Petek, et al., European J. Biochem. 8:395–402 (1969).
Distler, et al., J. Biol. Chem., 248:6772–6780 (1973).
Dey, et al., Biochimica et Biophysica Acta, 370:269–275 (1974).
Arakawa, et al., J. Biochem., 75:707–714 (1974).
Tanaka, et al., J. Biochem., 77:241–247 (1975).
Li, et al., J. Bio. Chem., 250:6786–6791 (1975).
Akasaki, et al. J. Biochem. 80:1195–1200 (1976).
Brandao, et al., J. Dairy Sci., 70:1331–1337 (1987).
Shigeta, et al., J. Biochem., 110:136–140 (1991).
Product Literature, "Tools For Glycobiology, Beta–Galactosidase, Catalog No. X–5008," Oxford GlycoSystems, Abingdon, England (1992).
Priyolkar, et al., Arch. Microbiol., 151:49–53 (1989).
Paulson, et al., J. Biol. Chem., 253:5617–5624 (1978).
Frost, et al., Biochem. 175:181–188 (1978).
Hubert, et al., J. Biochem., 213:275–278 (1983).
Johnson, et al., Arch. Biochem. Biophys. 138:408–411 (1970).
Pisani, et al., Eur. J. Biochem., 187:321–328 (1990).
Lo, et al., J. Biol. Chem. 254:6710–6715 (1979).
Kiyohara, et al., J. Biochem., 80:9–17 (1976).
John, et al., Hemicellulose, date unknown.
Matsuo, et al., Agric. Biol. Chem., 51:2367–2379 (1987).
Kitpreechavanich, et al., Agric. Biol. Chem., 50:1703–1711 (1986).
Shao, et al. J. Bacteriol. 174:5848–5853 (1992).
Dobberstein, et al., Appl. Microbiol. Biotechnol. 35:210–215 (1991).
Bachmann, et al., J. Gen. Microbiol. 135:293–299 (1989).
Buttner, et al., J. Basic Microbiology, 32:159:166 (1992).
John, et al., Can. J. Biochem., 57:125–134 (1978).
Yamashita, et al., Biochem. & Biophys. Res. Comm. 100:226–232 (1981).
Phyzackerley, et al. Biochemica et Biophysica Acta 362:129–135 (1974).
Mitchell, et al., Phytochemistry, 15:1869–1871 (1976).
Ortiz, et al., Biochimica et Biophys. Acta 289:174–186 (1972).
Agrawal, et al. J. Biol. Chem., 243:103–111 (1968).
Bahl, et al., J. Biol. Chem. 244:2970–2978 (1969).
Berg, et al., App. & Environ. Micro. 40:40–47 (1980).
Findlay, et al., Biochem. J. 77:170–175 (1960).
Kimura, Biochimica et Biophysica Acta 446:399–406 (1976).
St. Leger, et al., J. Inveterbrate Pathology, 58:415–426 (1991).
Robinson, et al. Biochem. J. 107:321–327 (1968).
Legler, et al., Biochimica et Biophysica Acta, 1080:89–95 (1991).
Mega, et al., J. Biochem. 68:109–117 (1970).
Ceccarini, et al., Eur. J. Biochem., 132:469–476 (1983).
Bedi, et al., Arch. Biochem. & Biophys. 233:237–250 (1984).
Verpoorte, Biochemistry, 13:793–799 (1974).
Frohwein, et al., Biochemistry 6:2775–2782 (1967).
Verpoorte, J. Biol. Chem., 347:4787–4793 (1972).
Bedino, et al., "Comparative Study of Glycosidases From The Thermophilic Fungus Thermoascus Aurantiacus Miehe. Purification And Characterization of Intracellular Beta–Glucosidase" (Need Citation).
Imai, J. Biochem., 98:1405–1416 (1985).
Deshpande, et al., Eur. J. Biochem., 90:191–198 (1978).
Cruzet, et al., Biochem & Biophys. Res. Comm. 90:537–546 (1979).
Yague, et al., Eur. J. Biochem., 175:627–632 (1988).
Shewale, et al., Arch. Biochem. & Biophys. 207:185–196 (1981).
Hosel, et al., Hoppe–Seyler's Z. Physiol. Chem. Bd. 358:959–966 (1977).
Hidalgo, et al., Biotech. & App. Biochem. 15:185–191 (1992).
Sengupta, et al., Biochimica et Biophysica Acta, 1076:215–220 (1991).
Chirico, et al., Eur. J. Biochem., 165:333–341 (1987).
Painbeni, et al., J. Bacteriology, 17:3087–3091 (1992).
Freer, Arch. Biochem. Biophys. 243:515–522 (1985).
Vimr, et al., J. of Bacteriology, 170:1495–1504 (1988).
Lee and Forsberg, Appl. and Environ. Micro., 54:651–654 (1987).
Panbangred, et al., Eur. J. Biochem., 138:267–273 (1984).
Bachmann and McCarthy, J. of Gen. Micro., 135:293–299 (1989).
Shao and Wiegel, J. Bacteriology 174:5848–5853 (1992).

Buttner and Bode, J. Basic. Microbiol. 32:159–166 (1992).

Dobberstein and Emels. Appl. Micro. Biotechnol., 35:210–215 (1991).

Garcia–Campayo, et al., Carbohydrate Research, 242:229–245 (1993).

Kersters–Hilderson, et al., Eur. J. Biochem., 7:434:441 (1969).

John, et al., Can. J. Biochem., 57:125–134 (1979).

John and Schmidt, Methods in Enzymology, 160:662–671 (1988).

Matsuo and Yasui, Methods in Enzymology 160:684–695 (1988).

* cited by examiner

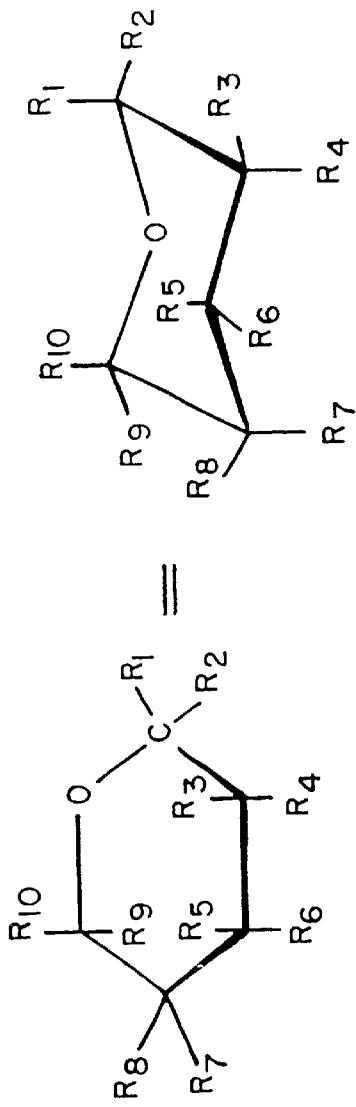
FIG. I

113 : Galβ1-3GlcNAcβ1-3Galβ1-4Glc-Co
        /
       Fucα1-4

167 : Galβ1-3GlcNAcβ1-3Galβ1-4Glc-Co

Substrate 113
1  +  no preparation
2  +  X. holcicola preparation
3  +  X. badrii preparation
4  +  X. manihotis preparation
5  +  X. cyanopsidis preparation
6  +  X. oryzae preparation
7  +  X. campestris preparation
8  +  X. campestris preparation Substrate 157
9   +  no preparation
10  +  X. holcicola preparation
11  +  X. badrii preparation
12  +  X. manihotis preparation
13  +  X. cyanopsidis preparation
14  +  X. oryzae preparation
15  -  X. campestris preparation
16  -  X. campestris preparation

FIG. 2

109 : Galα1-3Galβ1-3GlcNAc-Co

Substrate 109
Lanes 1-4 = complete digest
1 = 1 μl. of α1-3, 6 Galactosidase
2 = 0.5 μl.
3 = 0.25 μl. : concentration of enzyme-4 units/μl.
4 = 0.125 μl.
5-8 = partial digest
9-10 = undigested

ISOLATION AND COMPOSITION OF A NOVEL GLYCOSIDASE FROM CHRYSEOBACTERIUM

CROSS-REFERENCE TO RELATED APPLICATIONS

The present application is a Divisional Application of U.S. application Ser. No. 09/428,979 filed Oct. 28, 1999 which is a Continuation-In-Part of U.S. application Ser. No. 08/560,809 filed Nov. 21, 1995, now U.S. Pat. No. 6,300,113 which is a Continuation-In-Part of U.S. Ser. No. 08/596,250 filed Jun. 24, 1996, now U.S. Pat. No. 5,770,405, which is a 371 of PCT/US94/10758 filed Sep. 22, 1994 which claims priority of U.S. Ser. No. 08/126,174 filed Sep. 23, 1993, now abandoned.

TECHNICAL FIELD

The present invention relates to novel glycosidases and their uses.

BACKGROUND OF THE INVENTION

The recognition that carbohydrates play a key role in biological processes of living organisms has made their study of great importance for medicine and basic science. The understanding of carbohydrates has lagged behind that of other types of biological molecules because of the immense complexity and variety of these molecules and the lack of availability of analytic and synthetic tools that enable scientists to differentiate one form from another.

Forms of Carbohydrates in Nature.

In nature, carbohydrates exist as polymers known as polysaccharides, that consist of a series of monosaccharides that are covalently attached by glycosidic bonds to form both branched and linear macromolecules. In addition, polysaccharides or, more commonly, oligosaccharides may be coupled to macromolecules such as proteins or lipids to form glycoproteins or glycolipids. Unlike naturally occurring polysaccharides, the oligosaccharides associated with protein or lipid consist of a relatively small subset of monosaccharide types.

Oligosaccharides associated with glycoproteins have been the focus of much of the carbohydrate research to date largely because the biological properties of these molecules are diverse and their relatively short monosaccharide sequences make the oligosaccharides amenable to study.

Structural Features of Glycoproteins.

Glycoproteins are characterized into two groups according to their linkage to protein. The O-glycosyl linked oligosaccharides including mucin-type oligosaccharides, the proteoglycan type, the collagen-type and the extensin-type are bonded to the hydroxyl oxygen of L-serine or L-threonine. The N-glycosyl linked oligosaccharides are bound to the amido nitrogen of asparagine in a tripeptide generally of the form Asn-Xaa-Ser/Thr (where Xaa represents any amino acid). The N-linked oligosaccharides are further differentiated into 3 subgroups these being the high mannose type, the complex type and the hybrid type. N-linked oligosaccharides are frequently branched where branching commonly occurs either at a mannose residue or at an N-acetylglucosamine residue. These branched structures are called biantennary, if there are two branches, and triantennary if there are three branches.

The oligosaccharide can be characterized by its sequence of monosaccharides. The oligosaccharide is attached at its reducing end to the amino acid sequence of the protein while the non-reducing end is found at the terminal monosaccharide at the other end of the oligosaccharide. Other important characteristics of oligosaccharides are the glycosidic bonds that connect individual monosaccharides. The glycosidic bonds obtain their numerical assignment according to the carbons in the monosaccharide ring where linkage occurs. The carbons are numbered in a clockwise direction from 1 to 6. Any of these carbons can be involved in the glycosidic bond although commonly the carbon-1 on the monosaccharide closer to the non-reducing end forms a glycosidic bond with any other carbon on the monosaccharide toward the reducing end of the oligosaccharide. Because each carbon on a monosaccharide is asymmetric, the glycosidic bond occurs in two anomeric configurations, the alpha and the beta anomer. The type of anomer is determined by the position of the reactive hydroxyl group on the carbon. FIG. 1 illustrates the possible linkage configurations that may exist between two monosaccharides.

Synthesis and Degradation of Oligosaccharides.

Oligosaccharides are synthesized by a battery of enzymes in the cell known as glycosidases and glycosyltransferases. Typically, an oligosaccharide is assembled on a lipid carrier and transferred to the appropriate amino acid within the protein to be glycosylated. Glycosidase trimming and glycosyltransferase mediated synthesis follows and individual monosaccharides or preassembled oligosaccharide units are removed or added. In addition, microscopic reversibility may occur when the exoglycosidases that are usually hydrolytic enzymes, act as transferases in a synthetic role (Ichikawa et al. 1992, Anal. Biochem. 202:215–238). In some cases, removal of a monosaccharide results in a conformational change that facilitates further chain synthesis (Camirand et al. 1992, J. Biol. Chem., 266:15120–15127). While not wishing to be bound by theory, one cause of inter-cellular variability in glycosylation patterns for a single protein may arise from different amounts and types of available glycosidases and glycosyltransferases in any single cell.

The availability of individual glycosidases and glycosyltransferases depends on the nutritional environment of the cell (Goochee and Monica 1990, Bio/Technology 6:67–71) the type of cell (Sheares and Robbins 1986, PNAS 83:1993) and its homeostatic state (Kobata 1988, Gann Monogr. Cancer Res. 34:3–13). Associated with the variation it amounts and type of these intracellular enzymes is the occurrence of multiple glycoforms of a single glycoprotein (Parekh et al. 1987, EMBO 6:1233–1244). These glycoforms differ in their oligosaccharide sequence and linkage characteristics as well as in the position and number of attachment sites of the oligosaccharide to the protein. Variation in glycosylation of a single glycoprotein made in different cell types is an important aspect of recombinant protein therapeutic production because of the possible impact of structural heterogeneity on biological function (Sasaki et al. 1987, J. Biol. Chem. 262:12059–12076; Dube et al. 1988, J. Biol. Chem. 263:17516–17521; Lund et al. 1993, Human Antib. Hybridomas, 4:20–25; Parekh et al. 1989, Biochem. 28:7644–7662; Kagawa et al. 1988, J. Biol. Chem. 263:17508–17515; Parekh et al. 1989, Biochem. 28:7662–7669; Parekh et al. 1989, Biochem. 28:7670–7679).

Not only does the glycosylation pattern of a single protein vary according to which cell it is synthesized within, but individual glycosylation events may be characteristic of certain evolutionarily related animal species only. Galili et al. 1987, Immunology 84:1369–1373 and Galili et al. 1988, J. Biol. Chem. 263:17755–17762 identified the occurrence of Galα1-3Gal in non-primate mammals and New World monkeys, a glycosylation pattern that was absent in humans and Old World monkeys. The absence of this structure could be demonstrated because the disaccharide elicits an immune response in humans. The immune response to atypical glycosylation patterns presents a yet unsolved antigenicity problem that arises from using glycoproteins derived or manufactured in non-primate sources.

Oligosaccharides are degraded by glycosidases that are often highly specific for the glycosidic linkage and the stereochemistry of the oligosaccharide. An example of the influence of remotely located monosaccharides on the digestion of oligosaccharides is found in human patients suffering from fucosidosis. These patients lack the exoglycosidase required to remove fucose from N-linked oligosaccharides prior to digestion with endoglycosidase. The fucose interferes with the enzymatic activity of the endoglycosidase and causes undigested oligosaccharides to be excreted in their urine. (Kobata 1984, *The Biology of Carbohydrates*, Eds., Ginsberg and Robbins, Wiley, N.Y. vol. 2, pp. 87–162.)

The Biological Impact of Glycosylation of Proteins.

The importance of correct synthesis and degradation of oligosaccharides for the organism has been demonstrated in diseases which result from a single defective glycosidase giving rise to incorrect processing of carbohydrate structures. In the example cited above, disease results from the absence of a Fucosidase resulting in incorrect processing of the glycoprotein. Other examples include human α-Mannosidosis in which the major lysosomal α-Mannosidase activity is severely deficient (Gasperi et al. 1992, *J. Biol. Chem.* 267:9706–9712). Aberrant oligosaccharide structures have also been associated with cancer (Sano et al. 1992, *J. Biol. Chem.* 267:1522–1527).

The oligosaccharide side chains of glycoproteins have been implicated in such cellular processes as protection of peptide chains against proteolytic attack, facilitation of secretion to the cell surface, induction and maintenance of the protein conformation in a biologically active form, clearance of glycoproteins from plasma and antigenic determinants in differentiation and development. In fact, at any developmental stage, cells may have solved the biosynthetic problem of controlled variation by making not just one glycoprotein but by coding for large repertoires of a protein, each variant having a different covalently attached oligosaccharide (glycoform). The extent of variability that arises from multiple glycosylation sites on a peptide or indeed multiple forms of a single glycosylation site have been discussed by Rademacher et al. 1988, *Ann. Rev. Biochem.* 57:785–838, for recombinant proteins. Because the characteristics of glycoprotein as well as its biological properties and function vary according to the sequence and structure of the attached oligosaccharides (Cumming 1991, *Glycobiology* 1:115–130), the analysis of glycoprotein structure has become an important requirement in characterizing recombinant pharmaceutical proteins.

New methods of analyses are required to facilitate quality control of manufactured pharmaceutical grade recombinant protein to permit rapid, low cost and reliable characterization of oligosaccharides to distinguish between closely related structures (Spellman 1990, *Anal. Chem.* 62:1714–1722). New methods to manipulate and modify oligosaccharides on glycoproteins is desirable to improve production levels from cells and to optimize the biological function of proteins as therapeutic agents.

A method has been developed to modify blood sugar groups by using specific exo-glycosidases (Goldstein et al. 1989, *Trans. Med Rev.* 3:206–212). The enzymatic conversion of A and B erythrocytes to group O may lead to a universal pharmaceutical reagent that can be used for transfusion therapy.

A rapid and simple method of oligosaccharide sequence and linkage analysis would have utility in directing synthesis and analyzing function of glycoproteins and carbohydrates in general as well as providing insights into the causes and implications of microheterogeneity in glycosylated molecules made in different organisms, organs or cells as well as within a single cell.

Methods of Analyzing Carbohydrate Structures.

Existing methods for analyzing carbohydrate structure rely on complex multi-step procedures. These procedures involve techniques such as mass spectrometry, NMR, fast atom bombardment, complex chromatography techniques (high pressure liquid chromatography, gas phase chromatography, ion-exchange and reverse-phase chromatography) and complex series of chemical reactions (methylation analysis, periodate oxidation and various hydrolysis reactions) and have all been used in various combinations to determine the sequence of oligosaccharides and the features of their glycosidic linkage. Each method can provide certain pieces of information about carbohydrate structure but each has disadvantages. For example, fast atom bombardment (Dell 1987, *Advances in Carbohydrate Chemistry and Biochemistry* 45:19–73) can provide some size and sequence data but does not provide information on linkage positions or anomeric configuration. NMR is the most powerful tool for analyzing carbohydrates (Vliegenthart et al. 1983 *Advances in Carbohydrate Chemistry* 41:209–375) but is relatively insensitive and requires large quantities of analyte. These methods have been reviewed by Spellman 1990, *Anal. Chem.* 62:1714–1722; Lee et al. 1990, *Applied Biochem. and Biotech.* 23:53–80; Geisow 1992, *Bio/technology* 10:277–280; Kobata 1984. Many of the above procedures require expensive equipment as well as considerable technical expertise and technical support for their operation that limits their use to a few specialist laboratories.

Carbohydrate Analyses Using Glycosidases.

Enzymes have been used at various stages of carbohydrate analysis as one step in the multi-step analyses. These enzymes include glycoamidases having the ability to cleave between the glycan portion and the amino acid (commonly Asparagine) of the protein with which it is associated. Most important are the endoglycosidases and exoglycosidases which are both hydrolases and are so named because of their ability to specifically cleave glycosidic bonds either within the carbohydrate structure (endo-) or at the terminal monosaccharides (exo-) at the non-reducing end of the molecule.

Endoglycosidases have been described that cleave oligosaccharides at the reducing end at the penultimate monosaccharide to the amino acid attachment site on the peptide. Five endo-β-N-Acetylglucosaminidases have been purified sufficiently for use in structural studies each having a different substrate specificity (Kobata 1984). In addition, an endo-α-N-acetylgalactosaminidase has also been isolated (Umemoto et al. 1977, *J. Biol. Chem.* 252:8609–8614; Bhavanandan et al. 1976, *Biochem. Biophys. Res. Commun.* 70:738–745). The specificity of these endoglycosidases make them powerful tools in analyzing oligosaccharide structure. At this time, endoglycosidases have limited applicability due to the small number of characterized enzymes currently commercially available. An increased number of characterized endoglycosidases having different specificities would be of utility in carbohydrate analyses.

Oligosaccharides released by endoglycosidase digestion or by chemical means may be further characterized by exoglycosidase digestion. Exoglycosidases are hydrolases that cleave monosaccharide units from the non-reducing terminus of oligosaccharides and polysaccharides. Because exoglycosidases have known specificities for different terminal monosaccharides as well as for different anomeric forms, they have been used to sequence oligosaccharides. Sequential exoglycosidase digestion used in conjunction with gel permeation chromatography was first described by Yashita et al. in 1982 (*Methods in Enzymology* 83:105–126). Edge et al. (1992, *PNAS* 89:6338–6342) described multiplex enzyme reaction digestions and analysis of a sequence by analysis of arrays of enzyme digestions. The power of sequencing oligosaccharides using glycosidases has been limited by the availability of enzymes with well-characterized substrate specificities. The limitations of substrates for analyzing glycosidase activity has also resulted in incomplete data on glycosidic linkages between monosaccharides. As a result, it has been necessary to conduct methylation analysis to determine glycosidic linkages subsequent to sequence analysis.

Exoglycosidases have been isolated from diverse sources including bacteria, viruses, plants and mammals and have specificities for sialic acid ($\alpha$ anomer), galactose ($\alpha$ and $\beta$), N-acetylglucosamine ($\alpha$ and $\beta$), N-acetylgalactosamine ($\alpha$ and $\beta$), mannose ($\alpha$ and $\beta$) (Sano et al. 1992, *J. Biol. Chem.* 267:1522–1527; Moremen et al. 1991, *J. Biol. Chem.* 266:16876–16885; Camirand et al. 1991, *J. Biol. Chem.* 266:15120–15127; Gasperi et al. 1992, *J. Biol. Chem.* 267:9706–9712; Ziegler et al. 1991, *Glycobiology* 1:605–614; Schatzle et al. 1992, *J. Biol. Chem.* 267:4000–4007).

Glycosidases in the prior art have been defined in most examples by their substrate specificity where the characterization of the enzyme is limited by the availability of suitable substrates and the complexity of the assay. Furthermore, enzymes in the prior art are frequently named in an arbitrary fashion, where the names suggest biological activities that have never been demonstrated. Limitations in the characterization of crude extracts or purified enzymes arise in the prior art because of the lack of suitable assays that identify what substrates are cleaved and what substrates are not cleaved by any single enzyme. Associated with the problems of characterizing the enzymes are problems associated with identifying contaminating glycosidase activity. Furthermore, not only are glycosidase preparations commonly contaminated with other glycosidases they are also contaminated with proteases. The limitations in characterizing enzymes cited in the prior art and the difficulties in obtaining substantially pure preparations of glycosidases is reflected in the sparsity of the list of commercially available glycosidases (see Table 1).

The substrates most commonly used in the prior art are derivatized monosaccharides (p-nitrophenyl-monosaccharide or 4-methylumbelliferyl monosaccharide). Whereas these substrates may provide information on some of the monosaccharides that are recognized by glycosidases, no information on glycosidic bond cleavage specificities can be obtained because the monosaccharide is chemically linked to the chromogenic marker and is not linked through a glycosidic linkage to a second monosaccharide. In addition the derivatized substrates are of limited use in characterizing the recognition site of a glycosidase. Glycosidases that cleave the monosaccharide derivative, do not always cleave the same monosaccharide in an oligosaccharide. Likewise, glycosidases that cleave an oligosaccharide may not cleave a derivatized substrate (Gasperi et al. 1992, *J. Biol. Chem.* 267:9706–9712).

A systematic approach is required to develop a set of labelled oligosaccharides suitable for characterizing the recognition site and the glycosidic cleavage site of a glycosidase. In addition to providing suitable substrates, simple rapid methods of analyzing the products of a single or multiple glycosidase reaction are required to accomplish the screening of a single glycosidase against multiple substrates or of multiple glycosidases against a single substrate.

Many of the glycosidases that are currently available have important limitations as analytic reagents (Jacob, et al., 1994, *Methods Enzymol*. 230:280–299). These include the following:

1) Contamination of exoglycosidase preparations with other exoglycosidase impurities that results in ambiguous digestion results.
2) Lack of specificity of the exoglycosidase for a specific glycosidic linkage. Glycosidases that have been characterized appear to recognize multiple linkages, some of these linkages being preferentially recognized over others. It would be desirable to identify the extent of preference of any given glycosidase for a single linkage.

Furthermore, as analytic reagents, the repertoire of available exoglycosidases of varying specificities does not provide sufficient range to analyze and differentiate many of the linear or branched structures that occur in nature.

Of the available glycosidases, there is a deficit of substantially pure highly specific enzymes that have defined and reproducible substrate specificities to perform carbohydrate analyses. The deficiency in the availability of these enzymes for carbohydrate analyses is caused at least in part by the lack of available techniques to isolate novel glycosidases and to characterize their substrate specificities. The availability of a wide range of glycosidases that have defined monosaccharide and glycosidic linkage preferences would eliminate the existing requirement for additional types of analysis such as methylation analysis to fully characterize an oligosaccharide and would provide a powerful tool in rapid characterization of novel carbohydrate structures and their biological properties.

Source of Exoglycosidases.

A limited number of exoglycosidases are commercially available (see Table 1). In addition, a large number of exoglycosidases have been isolated from a variety of organisms as described above. A partial list of exoglycosidases known to be useful for sequence determinations is provided by Linhardt et al. 1992, Intn'l Publ. No. WO 92/02816. An additional list of exoglycosidases is provided by Haughland 1993, Intn'l Publ. No. WO/93/04074. A comprehensive review of glycosidases is provided by Conzelman et al. 1987, *Adv. in Enzymol*. 60:89; Flowers et al. 1979, *Adv. in Enzymol*.48:29; Kobata 1979, *Anal. Biochem.* 100:1–14.

Although glycosidases that are presently available have been generally isolated and manufactured from natural sources, Schatzle et al. 1992, *J. Biol. Chem.* 267:4000–4007, has reported cloning and sequencing the lysosomal enzyme $\alpha$-Mannosidase isolated from *Dictyostelium discoideum*. Although Schatzle et al. characterized the structural properties of the enzyme, the substrate specificity with regard to glycosidic linkages was not revealed.

For the foregoing reasons, there is a need for novel substantially pure glycosidases suitable as reagents having defined substrate specificities and where the purified enzyme preparations are in a form that provides reproducible cleavage activity. Furthermore, there is a need for methods of isolating and manufacturing a wide array of these enzymes suitable for analyzing the wide variety of carbohydrate structures that occur in nature. Furthermore, there is a need for rapid, low cost, simple methods of carbohydrate analysis so as to characterize the substrate specificities of the enzymes; to provide rapid low cost methods of sequencing carbohydrate structures; and to modify carbohydrate moieties on glycoproteins and glycolipids for purposes of altering the biological properties of such molecules. The availability of a rapid, low cost, simple method of carbohydrate analysis would provide many opportunities to analyze the wide variety of carbohydrate structures that occur in nature, to understand the functions of these molecules and to modify their biological properties for useful purposes by manipulating their structures.

TABLE 1

COMMERCIALLY AVAILABLE GLYCOSIDASES

| ENZYME | SOURCE | LINKAGE SPECIFICITY |
|---|---|---|
| β-N-Acetylglucosaminidase | | |
| | Streptococcus pneumoniae[G,BMB] | 1–2,3 > 4,6 (+ GalNAc) |
| | Chicken liver[G] | 1–3,4 (+ GalNAc) |
| | Bovine kidney[BMB] | ? (+ GalNAc) |
| α-Fucosidase | | |
| | Almond meal[G] | 1–3, 4 |
| | Streptomyces sp142[T] | 1–3, 4 |
| | Arthrobacter[T] | 1–2 |
| | Chicken liver[G] | 1–2, 4, 6 |
| | Fusarium oxysporium[S] | 1–2, 4 |
| | Bovine epididymis[G] | 1–6 >> 2, 3, 4 |
| | Bovine kidney[BMB] | ? |
| α-Galactosidase | | |
| | Cottee bean[BMB,G] | 1–3, 4, 6 |
| | Mortieralla vinacea[S] | 1–4, 6 |
| β-Galactosidase | | |
| | Streptococcus pneumoniae[G,BMB,S] | β1–4 |
| | Bovine testes[BMB,G] | 1–3, 4 > 6 |
| | Jack bean[S,G] | 1–3, 4 > 6 |
| | Chicken liver[G] | 1–3, 4 |
| α-Mannosidase | | |
| | Jack bean[BMB,S,G] | 1–2, 6 >3 |
| | Aspergillus saitoi[G] | 1–2 |

[BMB]Boehringer Mannheim
[G]Glyko
[S]Seikagaku
[T]Takara

SUMMARY OF THE INVENTION

In accordance with the present invention, there is provided a composition comprising a substantially pure glycosidase obtainable from the genus Chryseobacterium, formerly known as Flavobacterium (1980, *Int. J. Syst. Bacteriol.* 30:225–420). More specifically, a substantially pure α-N-acetylgalactosaminidase having a substrate specificity for a GalNAcα1-X is provided. Also provided by the present invention is a recombinant Chryseobacterium glycosidase that is cloned by isolating DNA from a first organism, forming a gene library from the DNA in a second organism and identifying recombinant clones of the second organism having glycosidase activity.

BRIEF DESCRIPTION OF THE DRAWINGS

The foregoing aspects of the invention will become better understood with regard to the following description, appended claims and accompanying drawings where:

FIG. 1 shows the possible glycosidic linkages that may be formed between two monosaccharides.

FIG. 2 shows the characterization of purified *Chryseobacterium meningosepticum* α-N-Acetylgalactosaminidase using substrates 108 and 2–144.

DETAILED DESCRIPTION OF SPECIFIC EMBODIMENTS

Figure 3:
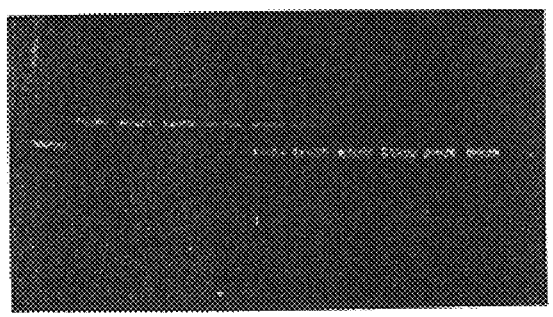
FIG. 3 shows the results of incubating crude extracts of Chryseobacterium with oligosaccharide substrates 108 to determine the presence of glycosidic activity.

"Substrate specificity" of a glycosidase is defined here and in the following claims as the ability of the glycosidase to recognize a specific monosaccharide or oligosaccharide and to cleave a characteristic glycosidic linkage positioned in a carbohydrate structure.

"A glycosidase" is defined here and in the claims as an enzyme that can catalyze the hydrolysis of the glycosidic linkage between two adjacent monosaccharides (wherein the monosaccharides occur within oligosaccharides, polysaccharides or in complex carbohydrates such as glycoproteins and glycolipids).

"Carbohydrate" is defined here and in the claims to denote oligosaccharides, polysaccharides or complex structures, these molecules either occurring freely or attached to a second molecule such as a protein or lipid.

"Oligosaccharide" is defined here and in the claims as a series of linked monosaccharides having a chain length in the range of two or more monosaccharides to approximately 30 monosaccharides.

"1-X" is defined here and in the claims as a linkage between the carbon 1 of a specified monosaccharide and an unspecified carbon on an adjacent unspecified monosaccharide.

"1-3R" is defined here and in the claims as a linkage between a carbon 1 on a specified monosaccharide (the unspecified monosaccharide "R" occurring within an oligosaccharide). Other linkages to carbon atoms other than to carbon 3 can be used as long as they are specified.

"A preparation from an organism" is defined here and in the claims as including cell extract or media.

Abbreviations have been used as follows: Glc is glucose, Gal is galactose, Fru is fructose, Man is mannose, GlcNAc is N-acetylglucosamine, GalNAc is N-acetylgalactosamine, Xyl is xylose, Fuc is fucose, β-GlcNAcase is β-N-Acetylglucosaminidase, β-GalNAcase is β-N-Acetylgalactosaminidase, β-Glcase is β-Glucosidase, and Co is coumarin, AMC is 7-amino methylcoumarin, TLC is thin layer chromatography.

Assay for Glycosidic Activity

The Chryseobacterium glycosidases of the present invention are assayed by a method that allows the rapid, simple and accurate determination of the digestion products of a glycosidase reaction. These methods are carried out as described in U.S. Pat. No. 5,770,405 (the disclosure of which is hereby incorporated by reference herein). The assay method is sufficiently sensitive to allow detection of contaminating enzyme activity (U.S. Pat. No. 5,770,405, supra. at FIG. 7), for determining enzyme titers by serial dilution (supra. at FIG. 3), and for determining relative affinities of a single enzyme for single and multiple glycosidic linkages (supra. at Example 4, FIGS. 2, 4–11).

Labelled Substrates Suitable for Screening for Glycosidase Activity.

Several approaches exist for labeling substrates to determine glycoside activity, as previously discussed at length (U.S. Pat. No. 5,770,405, supra). These include: chromogenic monosaccharide derivatives, fluorescently labelled oligosaccharides, and radioactively labelled oligosaccharides.

In a preferred embodiment of the invention, the fluorescent chromophore, 7-amino-4-methyl-coumarin (AMC) was selected for labelling oligosaccharide substrates at the reducing end. Advantages of AMC labelling include the following: high quantum efficiency and excellent photostability; little or no inhibitory effect on enzymatic cleavage of glycosidic linkages that are more than 1 monosaccharide removed from the reducing end; and ready detectability of the chromophore labelled oligosaccharide on a thin layer chromatogram. To optimize the separation of AMC-labeled oligosaccharides ranging in size from 1 to 30 carbohydrate residues, polar solvent systems have been formulated for the optimization of the separation of unmodified oligosaccharides according to the invention (Table 2).

TABLE 2

POLAR SOLVENT FORMULATIONS SUITABLE FOR THE SEPARATION OF OLIGOSACCHARIDES OF DIFFERENT SIZES

| SOLVENT LABEL | ISOPROPANOL:ETH ANOL H$_2$O V:V:V: | OLIGOSACCHARIDE SIZE RESOLVED |
| --- | --- | --- |
| A | 2.5:1.0:0.5 | 1–6 |
| B | 2.0:1.0:1.0 | 7–10 |
| C | 1.8:1.0:1.2 | 10–15 |
| D | 1.4:1.0:1.6 | 15–20 |

Analysis of the Reaction Products of Glycosidases.

Once the labelled substrate(s) have been reacted with the glycosidase, the reaction products if any were characterized using a suitable separation method. These separation methods have been previously discussed (U.S. Pat. No. 5,770,405, supra).

In a preferred embodiment of the invention, thin-layer silica gel chromatography (TLC) has been selected as a rapid method of separating hydrolysis products of a glycosidase reaction, by their molecular weight and the number of hydroxyl groups and is capable of separating 7-aminomethyl coumarin labelled oligosaccharides of different lengths that can be readily detected under UV light (see U.S. Pat. No. 5,770,405, supra, at Example 2).

The sensitivity of the above technique has been demonstrated in previous Examples that reveal the existence of contaminating enzymes in commercially available substrates (see U.S. Pat. No. 5,770,405, supra at FIG. 7) and in examples that show that a single glycosidase may have increased affinity for one glycosidic linkage over another (see U.S. Pat. No. 5,770,405, supra at FIG. 8). The advantages of this method have also been discussed at length (see U.S. Pat. No. 5,770,405, supra at FIG. 2, Table 2).

The choice of AMC as the fluorescent marker and TLC as a separation methodology does not however preclude other markers or other separation techniques from being used to assay glycosidic activity according to the methods of the invention.

Screening and Characterization of Glycosidases.

The screening and characterization of the Chryseobacterium glycosidases of the instant invention is carried out as previously described (U.S. Pat. No. 5,770,405, supra). The method involves the analysis of the glycosidase hydrolysis products from crude preparations of the organism using labelled oligosaccharide substrates or derivatized monosaccharides that have a defined length, composition, and secondary structure. Subsequently, glycosidases are isolated and further characterized and their substrate specificities are further defined.

Screening Organisms for Novel Glycosidases.

An embodiment of the present invention is the recognition that Chyrseobacterium which utilize carbohydrates as a carbon source can represent a source of novel glycosidases. This feature has been previously exemplified with other organisms (U.S. Pat. No. 5,770,405, supra at Tables 3 and 4). A number of novel exoglycosidases were identified from Xanthomonas extracts following thin layer chromatography of reacted substrates (U.S. Pat. No. 5,770,405, supra at FIG. 2).

In accordance with the present invention, we have applied the random screening method previously described (see U.S. Pat. No. 5,770,405, supra at Tables 3,4) to reveal multiple enzyme activities in different strains of related organisms (Chryseobacterium, FIG. 3) which have been further characterized in a single strain of organism, an example being *Chryseobacterium meningosepticum* (also known as *Flavobacterium meningosepticum*). The invention is not limited in scope to *Chryseobacterium meningosepticum* which serves here as an example of the utility of the invention. Instead, the invention is applicable to the genus Chryseobacterium.

Production of Glycosidases

Chryseobacterium glycosidases identified in accordance with methods of the present invention and subsequently isolated, purified and further screened against selected substrates, may be further characterized by protein sequencing providing a partial or complete protein sequence and a DNA coding sequence for purposes of preparing recombinant forms of the enzyme In a preferred embodiment, a method is described for cloning Chryseobacterium glycosidases and for screening recombinant clones so as to identify and isolate clones (Example 3). The efficiency of isolating recombinant clones can be further improved by growing the recombinant library on specific food sources accessible only to those organisms expressing a specific glycosidases. An embodiment of such a screening substrate includes a disaccharide (see Example 3) or an oligosaccharide linked to pantothenic acid. The availability of cloned glycosidases having a known DNA sequence further permits the genetic engineering of these DNA sequences to form mutant enzymes having altered substrate specificities.

Within the general method for isolating glycosidases from Chryseobacterium, it is also possible to isolate endoglycosidases wherein the cell extracts are screened against appropriately labelled substrates. In addition, within the general method for cloning glycosidases, endoglycosidases may be cloned using appropriately labelled substrates.

Characterization of Glycosidase Activity

Subsequent to the identification of enzyme activity in a crude extract, the invention provides for the isolation and purification of the glycosidases by techniques known in the art and described more fully in Example 1 (for glycosidases derived from Chryseobacterium). Following the isolation and purification of glycosidases, further characterization of the enzyme by its substrate specificity was performed (see Example 2; FIG. 2). Cofactor determination and the optimal pH of the reaction was also as identified as described in Table 3 (as previously described, U.S. Pat. No. 5,770,405, supra. at Example 4).

The invention is by no means restricted in scope to the substrates or the enzymes described below. Indeed, novel enzymes resulting from the screening method described, provide the means to construct novel labelled oligosaccharide substrates which may be further used to analyze crude extracts of organism or cells in an iterative process.

Novel glycosidases isolated and characterized from Chryseobacterium according to this invention have been characterized by the following features.

(a) Selective substrate specificity for different monosaccharides. Glycosidases of the invention are capable of differentiating between stereoisomers of pyranose monosaccharides. In a preferred embodiment, the α-N-Acetylgalactosaminidase of the present invention has an affinity for α-N-Acetylgalactosamine (GalNAcα1-X) over α-N-Acetylglucosamine (GlcNAcα1-X) (Table 4).

(b) Ability to distinguish between anomeric forms of a single monosaccharide. Within the set of substrates assayed, a glycosidase has specificity for one anomeric form only (α or β) of a monosaccharide.

(c) Substrate specificity for selected glycosidic linkages. The glycosidase of the invention has demonstrated specificity for the following single glycosidic linkage (for example GalNAcα1-3R), No information is available for the or for GalNAcα1-XR (where X can equal 2, 4, or 6) since no oligosaccharides are availabe at this time.

Some of the α-hexosaminidases have a preference for cleaving substrates in a linear array (GalNAcα1-R) whereas other glycosidases are capable of cleaving at branch points in an oligosaccharide (GalNAcα1-3 (Fucα1-2)Galα1-R), The glycosidases of the invention provide reproducible cleavage profiles using available linear and branched oligosaccharide motifs (FIG. 2). Variations in cleavage patterns may arise if the substrate is associated with carbohydrate structures (monosaccharides, oligosaccharide or polysaccharides) or with proteins, lipids or synthetic markers that sterically affect enzyme activity.

The glycosidase described herein, is an α1-3 N-Acetylgalactosaminidase with an ability to cleave GalNAcα1-3R linkages at a branch point. Cleavage of branched GalNAcα1-3R has utility in reducing the immunogenicity of stored blood and the availability of an α-(1-3)N-Acetylgalactosaminidase that selectively cleaves this substrate, provides an approach to modifying the ABO reactivity of blood stored in blood banks. Among the glycosidases described above, the α1-3,6 Galactosidase has clinical importance because of its ability to cleave the antigenic Galα1-3R linkage that is commonly terminally positioned on recombinant glycoproteins manufactured in non-human cell lines. The removal of the Galα1-3R linkage would eliminate an undesirable immune response to recombinant therapeutic proteins.

The identification of Chryseobacterium α1-3,6 Mannosidase, α1-2,3 Mannosidase, the α1-3 Mannosidase and α1-6 Mannosidase would provide the ability to identify and sequence the antennary branches attached to specific mannose linkages in high mannose and hybrid structures, thereby providing significantly greater resolution of structure than previously possible by enzymatic methods.

Although it is not possible to screen a single novel glycosidase against all possible substrate variants, selected substrates that represent commonly occurring carbohydrate motifs have been used here to characterize Chryseobacterium glycosidases of the present invention. The analysis however does not exclude the possibility that a glycosidase of the invention is capable of recognizing an additional substrate not included in the screening assay. Alternatively, a glycosidase may fail to recognize a known substrate included in a moiety of a larger molecule because of steric effects resulting from distantly located molecules in the same structure.

Applications of Glycosidases

In another embodiment of the present invention, the combination of large numbers of isolated, substantially pure glycosidases, including Chryseobacterium glycosidases, having an identified substrate specificity together with a rapid and simple assay for identifying reaction products, provide an improved method for accomplishing the following applications:

(a) sequencing carbohydrate structures that occur either freely in nature or have been cleaved from proteins or lipids;

(b) modifying oligosaccharides on glycoprotein, glycolipid or carbohydrate molecules that occur freely in nature for purposes of identifying the biological role of the oligosaccharides or for altering the biological characteristics of the molecule, where the molecules include therapeutic proteins;

(c) purifying a desired glycosidase by column chromatography or other means that require analysis of fractions having glycolytic activity and allowing the detection of undesirable contaminating glycosidases;

(d) manufacturing processes that require degradation of naturally occurring carbohydrate structures such as cellulose from plant material for use in the paper industry;

(e) characterizing carbohydrate receptors on cells having a specificity for selected oligosaccharide ligands;

(f) investigating mechanisms of action for biological systems that rely on characteristic carbohydrate structures as described by Varki 1993, *Glycobiology* 3:97–130 where the cited applications are incorporated by reference.

To more easily perform the above methods, kits may be prepared wherein the kits include a set of glycosidic enzymes isolated from natural sources or by recombinant means (the recombinant form being manufactured by fermentation of transformed microorganisms or from transgenic animals and plants) being substantially pure and having identified substrate specificities suitable for sequencing carbohydrates. Such kits may include reagents either singly or together that are suitable for cleaving oligosaccharides from proteins, lipids or carbohydrates and adding a fluorescent label (coumarin) at the reducing end.

Additionally, kits may be prepared wherein the kits include a set of glycosidic enzymes isolated from natural sources or by recombinant means being substantially pure and having identified substrate specificities suitable for identifying the biological role of carbohydrate moieties or for altering the biological characteristics of the macromolecule including therapeutic proteins.

Additionally, kits may be prepared wherein the kits include sets of fluorescent labelled substrates such as coumarin labelled substrates suitable for rapidly assaying glycosidase activity during the purification of such enzymes by column chromatography or other means that require analysis of fractions having glycolytic activity.

Kits may be prepared wherein the kits include enzymes suited for industrial scale treatment of naturally occurring or synthetic carbohydrate structures.

The examples presented below are only intended as specific preferred embodiments of the present invention and are not intended to limit the scope of the invention, except as provided in the claims herein. The present invetnion encompasses modifications and variations of the methods taught herein which would be obvious to one of ordinary skill in the art. All references cited above and below are hereby incorporated by reference herein.

EXAMPLE 1

METHOD FOR PURIFICATION OF GLYCOSIDASES FROM *Chryseobacterium meningosepticum*.

Fermentation of *Chryseobacterium meningosepticum*.

*Chryseobacterium meningosepticum* strain NEB #956 (ATCC No. 13253) was grown in media consisting of 5 g/l yeast extract, 5 g/l tryptone, 5 g/l sodium chloride, 3 g/l potassium phosphate (monobasic), 0.5 g/l NaCl, and Sodium hdroxide added until the pH equals 7.2. The cells were incubated at 30° C. overnight or until late logarithmic stage with aeration and agitation. The cells were harvested by centrifugation and stored frozen at −70° C.

Preparation of Crude Extract.

All further procedures were performed either on ice or at 4° C. 107 grams of cell paste obtained above were suspended in 150 ml of Buffer A (25 mM Tris-HCl (pH 7.0), 1.0 mM EDTA). The cell suspension was sonicated with a large tip set at with an output level equal to 9 at 40% duty cycle. The suspension was sonicated for 3 minutes let sit on ice for one minute and this step was repeated 30 times. Release of protein was monitored for protein release by the BioRad microtiter assay. The cell suspension was centrifuged at 8,000 g for 30 minutes.

AMC-Labeling of Oligosaccharides

AMC-labelled oligosaccharide substrates were prepared as previously described (U.S. Pat. No. 5,770,405, supra. at Examples 1, 6). Briefly, 0.1 to 5.0 μmoles oligosaccharide was dissolved in 100 μl $H_2O$. The aqueous carbohydrate solution was added to a solution containing 300 μl methanol, 20 mg (0.11 μmole) AMC(Eastman Kodak-Rochester N.Y.), 35 mg (0.55 μmole) $NaCNBH_3$ and 41 μl glacial acetic acid. The mixture was sealed into a screw cap microfuge tube and heated in a dry block at 80° C. for 45 minutes. The reaction was loaded onto a G-25 column (2×50 cm) equilibrated with deionized water. The product was eluted with deionized water and 1 ml fractions were collected. Fractions were assayed for purity by carefully spotting (to form a band), 5 μl onto a silica gel 60 TLC plate. The plate was developed by TLC as described below. The appropriate fractions were pooled and concentrated by vacuum to approximately 0.1–1 μmole/ml. Stock solutions were stored at −20° C.

Purification of α-N-Acetylgalactosaminidase.

Glycosidases were separated and purified from crude cell extracts by utilizing a series of separation methods that differentiated the enzymes according to their hydrophobicity and their charge. Enzymes were subsequently assayed according to methods previously described (U.S. Pat. No. 5,770,405, supra at Examples 2,7) using co-factor conditions described in Table 3. Briefly, 1–5 μl of bacterial cell extract or cell growth media or partially purified extracts were added to a 10 μl reaction mixture containing 1 nanomole of AMC labelled substrate in 50 mM Na citrate buffer (see Table 3 for pH and cofactors). The reaction was incubated at 37° C. for a period in the range of 5 minutes to 20 hours. 2–3 μl of reaction was spotted in a band onto a silica gel TLC plate as described below. One unit of enzyme was defined as the amount of enzyme required to release 1 nmole of terminal monosaccharide from an oligosaccharide substrate at 37° C. in 1 hour. 2–3 μl (=0.25 nmoles substrate) of glycosidase digestion reaction were spotted in a tight band (0.5 cm wide lane) onto silica gel 60 TLC glass-backed plates (0.25 mm thick, 20×20 cm). The bands were completely dried with a hot air gun (temperature should not exceed 70° C.). The TLC plate was developed until the solvent front moved 10 cm, in various isopropanol: ethanol: $H_2O$ mixtures (Table, 2) depending on the oligosaccharide sizes. The bands were visualized with a hand-held 314 nm ultraviolet lamp. A minimum of 0.1 nmol of digestion product could be detected using this technique.

Controls included a marker consisting of an undigested disaccharide (92b) (Galβ1-4GlcNAc-Co) a tetrasaccharide (167) (Galβ1-3GlcNAcβ1-3Galβ1-4Glc-Co) and a hexasaccharide (197) Galβ1-4GlcNAcβ1-6(Galβ1-4GlcNAcβ1-3) Galβ1-4Glc-Co. Undigested substrate also served as a control.

The crude extract (150 ml) from above was loaded onto a column of DEAE Sepharose CL-6B (5.0×12.5 cm) equilibrated with Buffer A (25 mM Tris-HCl pH 7.0, 1.0. mM EDTA). The column was washed with 1000 ml of Buffer A followed by a linear gradient of NaCl formed with 1000 ml of Buffer A and 1000 ml of Buffer A containing 1 M NaCl. Fractions (21 ml) were collected at a flow rate of 3 ml/min. Fractions were assayed for α-N-Acetylgalactosaminidase activity as described above (see also, U.S. Pat. No. 5,770, 405, supra, at Example 2) using AMC-labelled substrate and TLC.

The peak of enzyme activity flowed through the column and was also detected in the first 150 ml of Buffer A wash. The flow through from the DEAE Sepharose column was collected and assayed for all other glycosidase activities as described above. After determining that other glycosidases were present, the DEAE flow through was dialized against Buffer B (25 mM Na phosphate pH 6.0, 1.0 mM EDTA). After dialyses the flow through was immediately applied to a column of SP Sepharose CL-6B (2.6×50 cm) equilibrated with Buffer B. The column was washed with 400 ml of Buffer B followed by a linear gradient of NaCl formed with 500 ml of Buffer B and 500 ml of Buffer B containing 1.0 M NaCl. Fractions (15 ml) were collected at a flow rate of 2 ml/min. Fractions were assayed for α-N-Acetylgalactosaminidase activity as described above. The peak of α-N-Acetylgalactosaminidase activity eluted from the SP-Sepharose column between 0.14 and 0.2 M NaCl.

Fractions containing α-N-Acetylgalactosaminidase activity were pooled and the enzyme was further purified as previously described (U.S. Pat. No. 5,770,405, supra. at Example 4, section D). The column flow through and wash (350 ml) from the SP-Sepharose column was collected and assayed for β1-3>>4 Galactosidase, α1-2,3 Mannosidase, β-Glucosidase and α1-3,4 Fucosidase activities as described above. Some of the enzyme activities were found in the column wash. 66.25 ml of 4M ammonium sulfate was added to the 200 ml SP-column pool with gentle stirring resulting in a concentration of 1 M ammonium sulfate. The pool was then applied to a column of Phenyl Sepharose (1.6×5.0 cm) equilibrated with Buffer C (25 mM TrisHCl pH 7.0, 1 M $(NH_4)_2SO_4$, 1.0 mM EDTA). The column was washed with 50 ml of Buffer C followed by a linear decreasing gradient of ammonium sulfate formed with 50 ml of Buffer C and 50 ml of Buffer C containing only 0.001 M $(NH_4)_2SO_4$. The column was finally washed with 20 ml Buffer C. Fractions (3 ml) were collected at a flow rate of 2 ml/min. Fractions were assayed for α-N-Acetylgalactosaminidase activity described above. The peaks of α-N-Acetylgalactosaminidase activity eluted from the column between 0.04–0.0M $(NH_4)_2SO_4$.

Fractions containing α-N-acetylgalactosaminidase activity were pooled and the enzymes further purified as previously described (U.S. Pat. No. 5,770,405, supra, at Example 4, sections E and F). The column flow through and wash from the Phenyl Sepharose column were collected and assayed for α1-3,4 Fucosidase, α- and β-galactosidases and α- and β-glucosidases activities as described above.

After dialysis overnight against Buffer A (25 mM TrisHCl pH 7.0, 1.0 mM EDTA), the enzyme pool (19 ml) was applied to a S-Sepharose high performance (1 ml) column equilibrated with Buffer A. The column was washed with 2 ml (0.5 ml/min) of Buffer A followed by a 2 ml of a linear gradient of NaCl (0.0 t0 0.5M) in Buffer A using an FPLC. Fractions (0.5 ml) were collected at a flow rate of 0.5 ml/min and assayed for α-N-Acetylgalactosaminidase activity as described above. The peak of enzyme activity was pooled and eluted between 0.005–0.9 M NaCl (labeled Pool B). Some activity was detected in the flow through and it was pooled separately (lableled Pool A). After dialysis overnight against Buffer B (25 mM Na phosphate pH 6.0 1.0 mM EDTA), the enzyme pools were loaded onto two separate S-Sepharose high performance (1 ml) columns equilibrated with Buffer B. The columns were washed with 2 ml (0.5 ml/min) of Buffer B followed by a 2 ml of a linear gradient of NaCl (0.0 to 0.5M) in Buffer B using an FPLC. The column flow-through was collected for each column and assayed for α-N-Acetylgalactosaminidase activity. The peak of enzyme activity for the column loaded with Pool A was eluted between 0.16–0.19 M NaCl. The peak of enzyme activity for the column loaded with Pool B was eluted between 0.22–0.25 M NaCl. The peak activity from the column loaded with Pool A were contaminated with 5% α1-4 glucosidase activity. The peak activity from the column loaded with Pool B had no contamination of any other glycosidase activity. After the addition of sodium azide to 0.02%, the enzyme pools was stored at 4° C. The yield of substantially pure enzyme was 500 units.

TABLE 3

DETERMINATION OF CO-FACTOR REQUIREMENTS FOR GLYCOSIDASE ACTIVITY

| ENZYME | SUBSTRATE | pH | Ca$^{++}$ |
|---|---|---|---|
| α-N-Acetyl-galacto-saminidase (Chryseo-bacterium) | (Fucα1-2)GalNAcα1-3Galα1-4Galβ1-4Glc-Co | 6.0 | — |

EXAMPLE 2

CHARACTERIZING Chryseobacterium α-N-Acetylgalactosaminidase.

8 units of α-N-Acetylgalactosaminidase (α-GalNAcase) purified, as described in Example 1, from Chryseobacterium meningosepticum was found to react with 0.5–1 nmol substrate in the absence of cofactors in 50 mM sodium citrate pH 6.0 although the enzyme was similarly active at a pH in the range of pH 5.5–6.0. Incubation was carried out for 1 hour at 37° C.

The results are summarized in Table 4. The α-GalNAcase from Chryseobacterium had no detectable activity for PNP-GlcNAc as compared to ther commercially enzymes which also have no activity for this substrate.

TABLE 4

COMPARISON OF α-HEXOSAMINIDASE ACTIVITIES ON PNP GlcNAC v. PNP GalNAc

| SOURCE | PNP GlcNAc OD 400 | PNP GalNAc OD 400 |
|---|---|---|
| Chryseobacterium meningosepticum | ND | >2.0 |
| Acremonium sp. | ND | >2.0 |
| Chicken liver | ND | >2.0 |

Assays were performed using 1 NEB unit of enzyme at 37° C. for 1 hour as defined in Example 1.
ND = not detectable
PNP substrate was 10 mM, reaction volume was 25 μl, reaction was stopped using 75 μl 0.2M sodium borate pH 9.8, and the resulting absorbance was read at OD 400.

EXAMPLE 3

CLONING OF EXOGLYCOSIDASE GENES.

The method for cloning of exoglycosidase genes is described using Chryseobacteria meningosepticum as the source of naturally occurring glycosidase. However, the method may be applied not only to this embodiment but to any Chryseobacteria organism in which the probability of finding at least one glycosidase has been determined as described above.

A. DNA Purification.

To prepare the DNA of, 15 g of cell paste was resuspended by shaking gently for 30 min in 200 ml of 0.1 M Tris-HCl, 0.15 M NaCL, 0.1 M EDTA pH 8.0. The suspension was divided into two 15.0 ml portions. 3 ml of a 10 mg/ml lysozyme in 0.1 M Tris-HCl, 0.1 M EDTA pH 7.6 was added to each portion and each was incubated for 15 minutes at 37° C. Added 100 ml of 1% SDS 0.1 M NaCl, 0.1M TrisHCl pH 9.0 was added to each portion. Extracted each portion three times with 100 ml phenol presaturated with 0.5 M TrisHCl pH 8.0. (presaturaton occurs when the molten phenol is extracted with equal volumes of the Tris buffer until the pH of the phenol layer is 8.0). After the phenol extraction, the portions were extracted once with equal volumes of chloroform/isoamyl alcohol (24:1; v:v). The two portions were then equally aliquoted into six 30 ml centrifuge tubes. The DNA was then precipitated by adding NaCl to 0.5M and layering 2 volumes ethanol on top. The precipitated DNA was spooled onto a glass rod. The spooled DNA was dipped in 70% ethanol/water and then transferred to 5 ml of 1/10 SSC (20×SSC=3M Nacl, 0.3M Na Citrate). RnaseB was then added to a final concentration equal to 5 mg/ml. The solution was incubate overnight at 37° C. overnight with gentle agitation. The DNA was extracted twice with 5 ml phenol presaturates with Tris buffer as described above. The DNA solution was finally extracted twice with 5 ml of chloroform/isoamyl alcohol (24:1; v:v). Ethanol (2:1 v:v) was added with 3 M Na acetate pH 6.0 to 0.5M The mixture was incubated for one hour at −70° C. The DNA was spooled onto a glass hook, dipped into 70% ethanol in water and finally redissolved in 3 ml 10 mM Tris, 1 mM EDTA pH 8.0 to a final concentration of approximately 100 μg/ml.

B. Partial Digestion.

The purified DNA was cleaved with Sau3AI to achieve partial digestion as follows: 100 μl of DNA at 100 μg/ml in 100 mM Bis Tris Propane-HCl pH 7.0, 10 mM MgCl$_2$, 100 mM NaCl, 1 mM dithiothreitol buffer with 100 μg/ml BSA was divided into one 200 μl aliquot and six 100 μl aliquots. To the 200 μl tube was added 1 ul or 4 units of Sau3AI. 100 μl was withdrawn from the first tube and transferred to the second tube to achieve 2.0 units Sau3AI and so on, each succeeding tube receiving half of the previous amount of Sau3AI. The tubes were incubated at 37° C. for 15 minutes, heat-treated at 72° C. for 15 minutes then subjected to electrophoresis in a 0.8% agarose gel in Tris-Borate-EDTA buffer. DNA fragments ranging in size from about 9 to 2 kb (3 of the partial digest show this range) were collected by electrophoresing into DEAE anion exchange of paper for 2 hr. The paper from each lane was separately washed two times with 150 µl of buffer containing 0.1M NaCl, 10 mM Tris pH 8.0 and 1 mM EDTA. Subsequently, the DNA was eluted from the paper by washing the paper 3 times with 200 µl of a buffer containing 1.0 M LiCl, 20% (v/v) etanol 10 mM Tris pH 7.5 and 1 mM EDTA. The resulting solution containing the DNA fragment was extracted with 300 µl phenol/chloroform followed by extraction with 300 µl chloroform and precipitated with 1 ml absolute ethanol by placing in a dry ice/ethanol bath for 15 min. The DNA was pelleted at 14K rpm for 5 min. The pellet was rinsed with 70% ethanol, air dried and resuspended in a final volume of 25 µl 10 mM Tris pH 8, and 1 mM EDTA. The purified fragments were used as described in step C below.

C. Ligation.

The fragmented DNA was ligated to pUC19 as follows: 3 µg of Sau3AI-partially digested *Chryseobacterium meningosepticums* DNA (2 µl) was mixed with 1.5 µg of BamHI-cleaved and dephosphorylated pUC19 (1 µl). 5 µl of 10× ligation buffer (500 mM Tris pH 7.5, 100 mM MgCl$_2$, 100 mM DTT, 5 mM ATP) was added, plus 41 μl of sterile deionized water to bring the final volume to 50 μl. One μl of concentrated T4 DNA ligase ($2\times10^6$ U/ml) was added and the mixture was incubated at 16° C. for 2 hours. Five μl of the ligation mixture was deionized by drop dialysis using a Millipore VS 0.025 μM filter. The DNA was then electroporated into *E. coli* XL1Blue. The *E. coli* was prepared for electroporation by growing up 1 L of cells to Klett 50–80 in L-broth. The cells were chilled on ice for 15 to 30 minutes and then pelleted in the cold at 4,000 rpm for 15 mins. The pellet was washed 2 times in ice cold sterile water and once in 10% glycerol. The washed pellet was resuspended in 1 to 2 ml of 10% glycerol to a final cell concentration of $3\times10^{10}$ cells per ml. The cells were frozen until needed in 100 μl aliquots at −70° C. To electroporate the DNA into the prepared cells, the cells were gently thawed and placed on ice. 40 μl of cells were mixed with 4 μl of the ligated and dialyzed DNA. The mixture was placed into a cold 0.2 cm electroporation cuvette. A pulse of electricity at 12.5 kv/cm with a time constant of 4–5 msec was applied to the DNA cell mixture. The *E. coli* was immediately diluted with 1 ml Rich broth, allowed to grow at 37° C. for 30 min. A 1/100 dilution into Rich broth was plated onto 150 mm LB-agar plates (100 ul/78.5cm$^2$) containing ampicillum (100 μg/ml). After overnight incubation at 37° C., clones expressing an exoglycosidase were screened as described below.

D. Screening for Exoglycosidase Clones.

To screen for clones which express an α-N-Acetylgalactosaminidase exoglycosidase activity one chromogenic indicator substrate was employed. The chromogenic substrate used was 4-methylumbelliferyl 2-acetamido-2 deoxy-α-D-galacto pyranoside (galNAc1-α-4MU) which was added to 0.8% v/v molten agarose in 50 mM Na citrate pH6.0 to a final concentration of 0.25 mg/ml. The molten solution was layered over the selective agar plates using 4 ml/78.5 cm after the transformed cells are plated and grown overnight on the agar. Any colony grown on agar plates containing a gene which expresses a α-N-Acetylgalactosaminidase will fluoresce blue when excited with a 360 nm UV light. Of the $9\times10^4$ colonies screened in this manner only two colonies fluoresced blue. Alternatively, the 4-methylumbelliferyl (4-MU) substrates can be sprayed on the surface of the selective plate at a concentration of 1 μg/ml after colonies have formed. After spraying or overlaying colonies producing active exoglycosidase were identified by viewing the colonies with long wave ultraviolet light (366 nm). A third method may use the colormetric substrate 5-Bromo-4-chloro-3-indoyl 2-acetamido-2-deoxy-α-D-galactose. This substrate can be added to the selective agar before plating and blue colonies will contain the gene expressing the α-N-Acetylgalactosaminidase.

DNA sequence of the positive clones confirmed that an open reading frame was present. Amino terminal protein sequencing of the enzyme purified from *C. meningosepticum* confirmed that the gene cloned coded for the correct protein.

(SEQ ID NO:1)

```
ATGGGCGCCT TAATTCCCTC GAGCACTTTA TTCAACaTTT
TCGATTTCAA CCCTAAAAAG GTAAgAATAG CTTTTaTCGC
tGTTGGTTTA CGTGGACAAA CtCACGTAGA AAATATGGCA
AGACGTGATG ATGTGGAGAT TGTAgCATTT GCAGATCCGG
ATCCTTACAT GGTTGGACGT GCACAGGAAA TTcTGAAAAA
GAATGGCAAG AAGCCTGCTA AAGTTTTTGG AAATGGTAAT
GACGATTACA AAAACATGCT TaAAGATAAA AATATTGATG
CtGTPTPTGT aTCATCTCCA TGGGAATGGC ACCACGAACA
TGGCGTAGCA GCTATGAAAG CTGGTAAAAT TGTCGGAATG
GAAgTTTCCG GTGCTATAAC ACTGGAGGAA TGTTGGGATT
ACGTAAAAGT ATCTGAACAA ACCGGAGTTC CGTTAATGGC
ATTAGAAAAT GTATGCTACA GACGCGATGT AATGGCTATC
CTGAATATGG TAAGAAAAGG AATGTTCGGA GAACTTGTTC
ACGGAACAGG AGGCTACCAG CACGATTTAA GACCAGTTTT
ATTCAACAGT GGCATCAATG GTAAAAACGG AGATGGTGTT
GAATTCGGAG AAAAAGCATT TAGTGAAGCC AAGTGGAGAA
CGAACCACTA TAAAAACAGA AACGGGGAAC TTTACCCTAC
TCATGGTGTT GGTCCATTGC ATACAATGAT GGATATTAAC
CGTGGAAACA GATTACTAAG ATTATCATCT TTTGCATCCA
AAGCAAGAGG ATTACATAAA TACATCGTGG ATAAAGGTGG
AGAAAGCCAT CCTAATGCAA AAGTAGAATG GAAACAAGGA
GATATTGTTA CCACTCAGAT CCAGTGTCAC AACGGAGAAA
CTATTGTATT AACACACGAT ACCAGCTTAC AAAGACCATA
TAACTTAGGA TTCAAAGTTC AAGGTACAGA AGGTCTTTGG
GAAGATTTCG GCTGGGGAGA AGCAGCACAA GGATTTATTT
ACTTCGAGAA GATTATGAAC CATTCTCACA GATGGGATAG
TTCTGAAAAA TGGATTAAAG AATATGATCA CCCTATGTGG
AAGAAGCATG AGCAGAAAGC TGTTGGTGCG GGTCATGGCG
GTATGGATTA CTTCTTAGAT AATACGTTCG TAGAATGTAT
```

```
TAAAAGAAAT GAAGCATTCC CGTTAGATGT CTATGATCTG

GCTACATGGT ATTCCATTAC TCCTCTTAGT GAAAAGTCTA

TCGCTGAAAA CGGTGCCGTT CAGGAAATTC CTGATTTTAC

AAACGGTAAA TGGAAGAATG CTAAAAATAC ATTTGCAATA

AATGACGACT ACTAA
```

A sample of E. coli ER2688 (pUC19-αGalNAcase) has been deposited with the American Type Culture Collection under the terms and conditions of the Budapest Treaty on Oct. 27, 1999 and been assigned Patent Deposit No. PTA-873.

What is claimed is:

1. Isolated DNA which codes for an exo α-N-Acetylgalactosaminidase, wherein the isolated DNA is obtainable from Chryseobacterium.

2. A recombinant DNA vector comprising a vector into which a DNA segment coding for the exo α-N-Acetylgalactosaminidase has been inserted.

3. Isolated DNA coding for the exo α-N-Acetylgalactosaminidase, wherein the isolated DNA is obtainable from ATCC Accession No. PTA-873.

4. A cloning vector which comprises the isolated DNA of claim 2.

5. A host cell transformed by the cloning vector of claims 2 or 4.

6. A method of producing a exo α-N-Acetylgalactosaminidase comprising culturing a host cell transformed with the vector of claim 2 or 4 under conditions suitable for expression of said glycosidase.

* * * * *

UNITED STATES PATENT AND TRADEMARK OFFICE
CERTIFICATE OF CORRECTION

PATENT NO. : 6,423,525 B1  Page 1 of 1
DATED : July 23, 2002
INVENTOR(S) : Landry It is certified that error appears in the above-identified patent and that said Letters Patent is hereby corrected as shown below:

Column 2,
Line 44, replace "variation it" with -- variation in --

Column 7,
Line 43, replace "$^{BMB}$Boehringer Mannheim" with -- BMB: Boehringer Mannheim --
Line 44, replace "GGlyko" with -- G: Glyko --
Line 45, replace "SSeikagaku" with -- S: Seikagaku --
Line 46, replace "TTakara" with -- T: Takara --

Column 16,
Line 5, replace "GlcNAC" with -- GlcNAc --

Column 17,
Line 64, replace "ml/78.5 cm" with -- ml/78.5cm$^2$ --

Signed and Sealed this

Twenty-sixth Day of November, 2002

Attest:

JAMES E. ROGAN
Attesting Officer *Director of the United States Patent and Trademark Office*

SEQUENCE LISTING

<160> NUMBER OF SEQ ID NOS: 1

<210> SEQ ID NO 1
<211> LENGTH: 1335
<212> TYPE: DNA
<213> ORGANISM: Chryseobacterium meningosepticum

<400> SEQUENCE: 1

```
atgggcgcct taattccctc gagcactttα ttcaacattt tcgatttcaa ccctaaaaag    60
gtaagaatag cttttatcgc tgttggttta cgtggacaaa ctcacgtaga aaatatggca   120
agacgtgatg atgtggagat tgtagcattt gcagatccgg atccttacat ggttggacgt   180
gcacaggaaa ttctgaaaaa gaatggcaag aagcctgcta agttttttgg aaatggtaat   240
gacgattaca aaacatgct  taaagataaa aatattgatg ctgtttttgt atcatctcca   300
tgggaatggc accacgaaca tggcgtagca gctatgaaag ctggtaaaat tgtcggaatg   360
gaagtttccg gtgctataac actggaggaa tgttgggatt acgtaaaagt atctgaacaa   420
accggagttc cgttaatggc attagaaaat gtatgctaca gacgcgatgt aatggctatc   480
ctgaatatgg taagaaaagg aatgttcgga gaacttgttc acgaacagg  aggctaccag   540 cacgatttaa gaccagtttt attcaacagt ggcatcaatg gtaaaaacgg agatggtgtt   600
gaattcggag aaaaagcatt tagtgaagcc aagtggagaa cgaaccacta taaaaacaga   660
aacggggaac tttaccctac tcatggtgtt ggtccattgc atacaatgat ggatattaac   720
cgtggaaaca gattactaag attatcatct tttgcatcca aagcaagagg attacataaa   780
tacatcgtgg ataaaggtgg agaaagccat cctaatgcaa agtagaatg  gaaacaagga   840 gatattgtta ccactcagat ccagtgtcac aacggagaaa ctattgtatt aacacacgat   900
accagcttac aaagaccata taacttagga ttcaaagttc aaggtacaga aggtctttgg   960
gaagatttcg gctggggaga agcagcacaa ggatttattt acttcgagaa gattatgaac  1020
cattctcaca gatgggatag ttctgaaaaa tggattaaag aatatgatca ccctatgtgg  1080
aagaagcatg agcagaaagc tgttggtgcg ggtcatggcg gtatggatta cttcttagat  1140
aatacgttcg tagaatgtat taaaagaaat gaagcattcc cgttagatgt ctatgatctg  1200
gctacatggt attccattac tcctcttagt gaaaagtcta tcgctgaaaa cggtgccgtt  1260
caggaaattc ctgattttac aaacggtaaa tggaagaatg ctaaaaatac atttgcaata  1320
aatgacgact actaa                                                    1335
```